United States Patent [19]

Bundy

[11] 4,156,087
[45] May 22, 1979

[54] 9-DEOXY-16,16-DIMETHYL-PGF$_2$ COMPOUNDS

[75] Inventor: Gordon L. Bundy, Portage, Mich.

[73] Assignee: The Upjohn Company, Kalamazoo, Mich.

[21] Appl. No.: 921,632

[22] Filed: Jul. 3, 1978

Related U.S. Application Data

[60] Continuation-in-part of Ser. No. 786,712, Apr. 11, 1977, abandoned, which is a division of Ser. No. 614,243, Sep. 17, 1975, Pat. No. 4,033,989.

[51] Int. Cl.$^2$ ............................................ C07C 177/00
[52] U.S. Cl. .................................. 560/121; 260/501.1; 260/501.17; 562/503
[58] Field of Search ........................ 560/121; 562/503; 260/501.1, 501.17

[56] References Cited

U.S. PATENT DOCUMENTS 3,894,009  7/1975  Sakai et al. ............................ 260/240

Primary Examiner—Robert Gerstl
Attorney, Agent, or Firm—Robert A. Armitage

[57] ABSTRACT

The present invention relates to novel 9-deoxy-16,16-dimethyl-PGF$_2$ compounds, which are prostaglandin analogs useful for the same pharmacological purposes as the corresponding prostaglandins. In particular, the instant compounds are particularly and especially useful as gastric anti-ulcer agents and are useful in stimulating the pregnant mammalian uterus.

5 Claims, No Drawings

9-DEOXY-16,16-DIMETHYL-PGF$_2$ COMPOUNDS

CROSS REFERENCE TO RELATED APPLICATIONS

The present application is a continuation-in-part of Ser. No. 786,712, filed Apr. 11, 1977, now abandoned, which is a division of Ser. No. 614,243, filed Sept. 17, 1975, issued as U.S. Pat. No. 4,033,989 on July 5, 1977.

BACKGROUND OF THE INVENTION

The present invention relates to novel 9-deoxy-16,16-dimethyl-PGF compounds, including the free acid, pharmacologically acceptable salt and ester forms of 9-deoxy-16,16-dimethyl-PGF$_2$.

9-Deoxy-PGF$_2$, in both acid and pharmacologically acceptable salt form is described in U.S. Pat. 3,984,009, issued July 8, 1975. This patent further provides a broad generic disclosure of other 9-deoxy-PGF$_2$-type compounds.

DESCRIPTION OF THE PREFERRED EMBODIMENTS

A disclosure of the preparation and pharmacological uses of 9-deoxy-16,16-dimethyl-PGF$_2$, its corresponding pharmacologically acceptable salts and esters, is described in U.S. Pat. No. 4,033,989, the disclosure of which is incorporated here by reference. In particular, the instant 9-deoxy-16,16-dimethyl-PGF$_2$ compounds are useful as gastric anti-ulcer and uterine stimulating agents, in accordance with the methods described in U.S. Pat. No. 4,033,989.

Further, the preferred method for preparing 9-deoxy-16,16-dimethyl-PGF$_2$, methyl ester, is described in the following example:

EXAMPLE 1

9-Deoxy-16,16-dimethyl-PGF$_2$, methyl ester

A. 6 g of PGF$_{2\alpha}$, methyl ester, 11,15-bis(tetrahydropyranyl ether) is dissolved in 66 ml of methylene chloride and cooled to $-20°$ C. with an ice methanol bath under a nitrogen atmosphere. Thereafter there is added in a single portion 0.26 ml of triethylamine and dropwise over 30 sec 0.90 ml of methanesulfonyl chloride. The ice bath is removed and the resulting mixture stirred for 45 min whereupon TLC analysis indicates the reaction to be complete. Thereafter the reaction mixture is poured into an ice-sodium bicarbonate-hexane mixture and extracted with additional hexane. The hexane extracts are then washed with water, diluted with a mixture of potassium bisulfate, ice, sodium bicarbonate, and brine; washed with sodium sulfate; and concentrated under reduced pressure to yield 16,16-dimethyl-PGF$_{2\alpha}$, methyl ester, 11,15-bis(tetrahydropyranyl ether), 9 mesylate.

B. The tetrahydropyranyl ethers of the reaction product of Part A (about 6 g) are hydrolyzed in a mixture of tetrahydrofuran (10 ml), acetic acid (60 ml), and water (24 ml), yielding 2.8 g of 16,16-dimethyl-PGF$_{2\alpha}$, methyl ester, 9 mesylate.

C. The reaction product of Part B (2.7 g) is dissolved in 25 ml of hexamethylphosphoramide. Thereafter at ambient temperature lithium bromide (about 1.5 g) is added until a saturated mixture is obtained. The resulting mixture is then poured into a water-brine mixture and extracted with ethyl acetate and hexane (60:40). The extracts are then washed with water and brine, dried over sodium sulfate, and concentrated under reduced pressure to yield 2.1 g of crude 9-deoxy-9$\beta$-bromo-16,16-dimethyl-PGF$_2$, methyl ester. Chromatography on 350 g of silica gel packed with 5 percent isopropanol in hexane yields 1.058 g of pure product.

D. A chromium perchlorate solution (prepared from 2.6 g of chromium metal finely divided and reacted with 50 ml of 2 M perchloric acid under a nitrogen atmosphere with vigorous stirring until the chromium metal is completely dissolved), 25 ml, is added to a solution of 4.17 ml of ethylene diamine in 125 ml of dimethylformamide in water (9:1). Stirring for 5 min at ambient temperature under a nitrogen atmosphere is followed by addition of 1.05 g of the reaction product of Part C and 10 ml of dimethylformamide in water (9:1). After stirring at ambient temperature for 30 min, the resulting mixture is poured into a mixture of ice, brine, water, potassium bisulfate, ethyl acetate, hexane, and extracted with a mixture of ethyl acetate and hexane (1:1). The organic extracts are then washed with water in brine, dried over magnesium sulfate, and concentrated under reduced pressure to yield 915 mg of crude title product. Chromatography on silica gel (80 g) packed and eluted with ethyl acetate in hexane (1:1) yields 658 mg of pure 9-deoxy-16,16-dimethyl-PGF$_2$, methyl ester. Characteristic NMR absorptions are observed at 5.7–5.2, 4.1–3.6, 3.4, 0.90, and 0.85$\delta$.

EXAMPLE 2:

9-Deoxy-16,16-dimethyl-PGF$_2$

The reaction product of Example 1 (350 mg) in methanol is combined with 10 ml of 1 N aqueous potassium hydroxide with stirring under a nitrogen atmosphere. After 4 hr the resulting mixture is poured into brine, acidified with 5 ml of 2 N potassium bisulfate and extracted with ethyl acetate. The ethyl acetate extracts are then washed with brine, dried over magnesium sulfate, and concentrated to yield pure title product (358 mg).

EXAMPLE 3:

A pregnant Rhesus monkey, a standard experimental animal for determining the uterine stimulating potency of prostaglandins and analogs thereof, is given intravenous dosages of the various prostaglandins and analogs listed below according to the procedure of Kimball, F. A., et al., Biol. Reprod. 13:42–49 (1975). The following results are obtained:

| Compound | Minimum Effective Dose (μg) |
| --- | --- |
| PGE$_2$ | 10–15 |
| PGF$_{2\alpha}$ | 100–150 |
| 9-Deoxy-PGF$_2$ | 100 |
| 9-Deoxy-16,16-dimethyl-PGF$_2$ | 1 |

I claim:

1. A prostaglandin analog of the formula

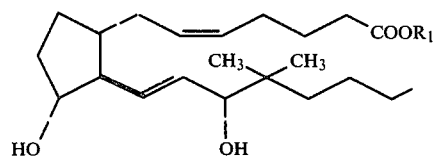

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 3 carbon atoms, inclusive, or a pharmacologically acceptable cation.

2. 9-Deoxy-16,16-dimethyl-$PGF_2$, methyl ester, a prostaglandin analog according to claim 1.

3. 9-Deoxy-16,16-dimethyl-$PGF_2$, tris(hydroxymethyl)aminomethane salt, a prostaglandin analog according to claim 1.

4. 9-Deoxy-16,16-dimethyl-$PGF_2$, adamantanamine salt, a prostaglandin analog according to claim 1.

5. 9-Deoxy-16,16-dimethyl-$PGF_2$, a prostaglandin analog according to claim 1.